US010343956B2

(12) United States Patent
Oleksy

(10) Patent No.: US 10,343,956 B2
(45) Date of Patent: Jul. 9, 2019

(54) PRODUCTION OF ALKYLAROMATIC COMPOUNDS

(71) Applicant: BADGER LICENSING LLC, Boston, MA (US)

(72) Inventor: Slawomir J. Oleksy, Billerica, MA (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 15/767,459

(22) PCT Filed: Oct. 15, 2015

(86) PCT No.: PCT/US2015/055690
§ 371 (c)(1),
(2) Date: Apr. 11, 2018

(87) PCT Pub. No.: WO2017/065771
PCT Pub. Date: Apr. 20, 2017

(65) Prior Publication Data
US 2018/0282242 A1 Oct. 4, 2018

(51) Int. Cl.
*C07C 2/66* (2006.01)
*C07C 7/04* (2006.01)
*C07C 15/085* (2006.01)

(52) U.S. Cl.
CPC ............ *C07C 2/66* (2013.01); *C07C 7/04* (2013.01); *C07C 15/085* (2013.01); *C07C 2529/70* (2013.01)

(58) Field of Classification Search
None
See application file for complete search history.

(56) References Cited

U.S. PATENT DOCUMENTS

| 4,324,941 A | 4/1982 | Ghirga et al. |
| 5,856,607 A * | 1/1999 | Kim ................... C07C 15/073 585/314 |

(Continued)

OTHER PUBLICATIONS

International Search Report and Written Opinion dated Mar. 18, 2016 in a corresponding application PCT/US2015/055690.

*Primary Examiner* — In Suk C Bullock
*Assistant Examiner* — Ali Z Fadhel
(74) *Attorney, Agent, or Firm* — Roberts Mlotkowski Safran Cole & Calderon, P.C.

(57) ABSTRACT

In a method for producing a monoalkylated aromatic product, benzene and an alkylating agent are contacted with an alkylation catalyst in a first alkylation reaction zone under alkylation conditions to produce a first alkylation effluent comprising the monoalkylated aromatic product, polyalkylated aromatic product, unreacted benzene and C5, C6 and/or C7 non-aromatic compounds. A purge stream containing C5, C6 and/or C7 non-aromatic compounds and unreacted benzene is removed from the first alkylation effluent and is contacted with an alkylating agent in a second alkylation reaction zone in the presence of an alkylation catalyst under alkylation conditions to produce a second alkylation effluent comprising monoalkylated aromatic product, polyalkylated aromatic product and C5, C6 and/or C7 non-aromatic compounds. The monoalkylated aromatic product is recovered from the first and second alkylation effluents and at least part of the C5, C6 and/or C7 non-aromatic compounds in the second alkylation effluent is purged.

15 Claims, 2 Drawing Sheets

(56) References Cited

U.S. PATENT DOCUMENTS

| | | | |
|---|---|---|---|
| 6,069,285 A * | 5/2000 | Fritsch | C07C 15/02 585/323 |
| 2002/0016520 A1 | 2/2002 | Paggini et al. | |
| 2008/0171900 A1 * | 7/2008 | Schmidt | B01J 29/70 585/449 |

* cited by examiner

US 10,343,956 B2

PRODUCTION OF ALKYLAROMATIC COMPOUNDS

CROSS-REFERENCE TO RELATED APPLICATIONS

The present application is a U.S. National Phase of PCT/US2015/055690 filed on Oct. 15, 2015. The disclosure of the PCT Application is hereby incorporated by reference into the present Application.

FIELD

This invention relates to the production of alkylaromatic compounds, particularly ethylbenzene (EB) and cumene.

BACKGROUND

Alkylaromatic compounds, such as ethylbenzene and cumene, are important intermediates in the chemical and polymer industries. For example, ethylbenzene is a commodity chemical used mostly for the production of styrene, whereas the majority of all cumene manufactured in the world today is used for the production of phenol. The demand for both ethylbenzene and cumene is rising.

Alkylaromatic compounds are typically produced by alkylating an aromatic compound, normally benzene, with an alkylating agent, typically an olefin, such as ethylene or propylene, under liquid phase or mixed gas-liquid phase conditions in the presence of an acid catalyst, particularly a zeolite catalyst. In addition to the desired monoalkylated aromatic compound, the process produces dialkylated aromatic compounds, some trialkylated compounds and other heavy by-products so it is conventional to transalkylate the polyalkylated species with benzene to increase the yield of the desired monoalkylated product. The effluent of the transalkylation reaction is then fed, together with the alkylation reaction product, to one or more benzene columns, to recover unreacted benzene, then to one or more alkylaromatic columns, to recover the desired alkylaromatic product. The unreacted benzene is recycled to the alkylator and/or transalkylator, normally after removal of water and lights ($C_4$ hydrocarbons) either in the top section of the benzene column or in a downstream benzene lights column which may also receive makeup benzene to the plant and the vapor distillate from the benzene column(s). The bottoms of the alkylaromatic column(s) are typically further distilled in one or more polyalkylated aromatic columns to recover most of the dialkylated aromatic component and part of the trialkylated aromatic component which are sent to the transalkylator for reaction with benzene to recover additional monoalkylaromatic compound. The remainder of the trialkylated aromatic component and essentially all of the heavier compounds are typically discharged at the bottoms of the polyalkylated aromatic column as residue. An aromatic purge is sometimes taken at the overhead of the polyalkylated aromatic column to remove lower molecular weight by-products (such as butylbenzenes and cymenes in the case of cumene production, or ethyltoluenes and propylbenzenes in the case of EB production) produced in the alkylator due to the presence of reactive impurities in the olefin feed and toluene in the benzene feed.

In many existing alkylaromatic plants, particularly cumene plants, a non-aromatic purge is included as well as the aromatic purge. The non-aromatic purge can be used to remove $C_5$, $C_6$ and/or $C_7$ non-aromatic impurities introduced into the system with the benzene feedstock and any non-aromatic compounds made in the alkylation and/or transalkylation reaction zones. Otherwise $C_5$, $C_6$ and/or $C_7$ non-aromatics can build up in the benzene recycle loop, which increases equipment cost and energy usage. Additionally, non-aromatics that are not purged can end up in the final alkylaromatic product, where their concentration must be controlled in accordance with the specifications set by the downstream product processing. The non-aromatic purge stream typically represents a yield loss of about 0.5 wt %, may contains up to 90 wt % benzene and is usually removed as a liquid distillate at the overhead of the benzene column or when present, from the top of the benzene lights column. The purge is then normally burnt as fuel or sold to a refinery at a heavily discounted price compared to the value of the contained benzene.

According to the present invention, it has now been found that the yield loss associated with the non-aromatic purge in an aromatics alkylation process can be significantly reduced by alkylating the benzene in the non-aromatics purge in a second alkylation reaction zone, separate from the main alkylation reaction zone, to produce additional monoalkylated and polyalkylated products. After separation of the non-aromatics and the unreacted benzene, the monoalkylated product can then be used to supplement the product obtained in the main alkylation reaction zone, whereas the polyalkylated products can be converted to monoalkylated product in the transalkylation reaction zone together with the polyalkylated benzenes produced in the main alkylation reaction zone.

SUMMARY

In one aspect, the invention resides in a method for producing a monoalkylated aromatic product, the method comprising:

(a) contacting benzene and an alkylating agent with an alkylation catalyst in a first alkylation reaction zone under alkylation conditions to produce a first alkylation effluent comprising the monoalkylated aromatic product, polyalkylated aromatic product, unreacted benzene and $C_5$, $C_6$ and/or $C_7$ non-aromatic compounds;

(b) removing a purge stream containing $C_5$, $C_6$ and/or $C_7$ non-aromatic compounds and unreacted benzene from the first alkylation effluent;

(c) contacting at least part of the purge stream with an alkylating agent in a second alkylation reaction zone in the presence of an alkylation catalyst under alkylation conditions to produce a second alkylation effluent comprising monoalkylated aromatic product, polyalkylated aromatic product and $C_5$, $C_6$ and/or $C_7$ non-aromatic compounds;

(d) recovering the monoalkylated aromatic product from the first and second alkylation effluents; and (e) purging at least part of the $C_5$, $C_6$ and/or $C_7$ non-aromatic compounds in the second alkylation effluent.

DETAILED DESCRIPTION OF THE EMBODIMENTS

DETAILED DESCRIPTION OF THE EMBODIMENTS

Figure 1:
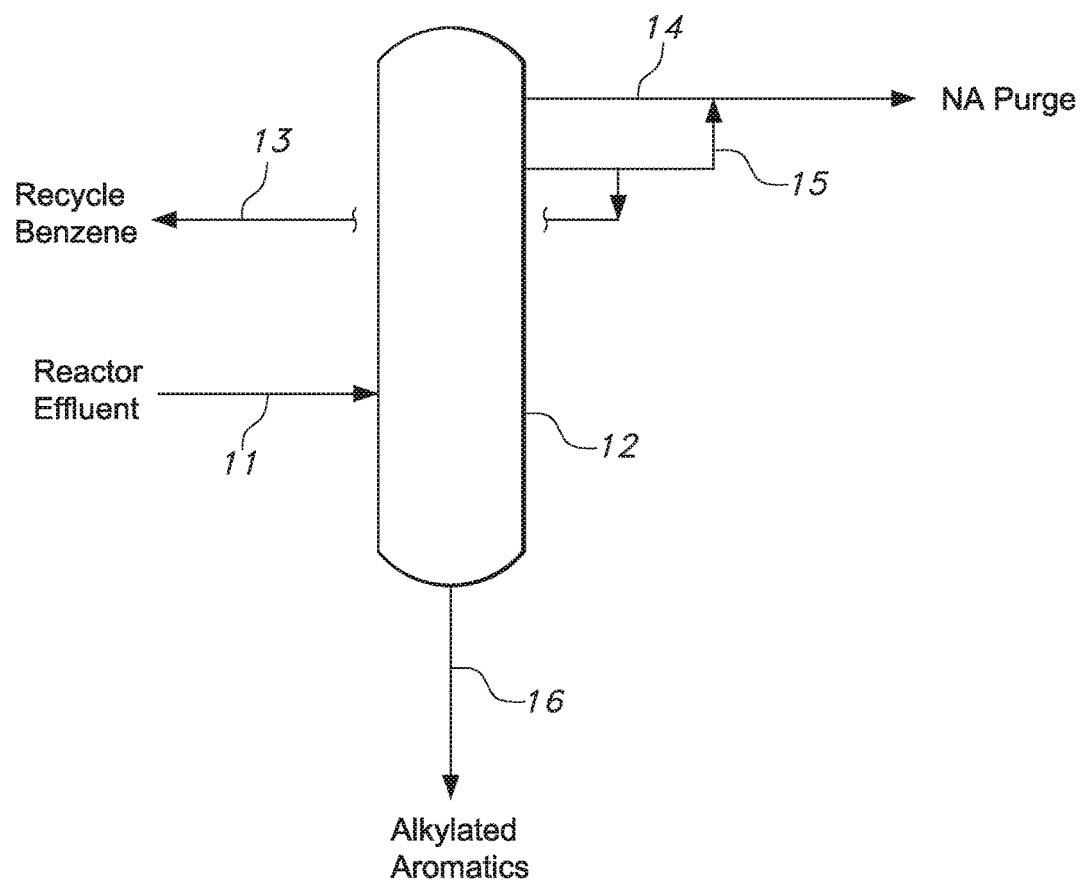
FIG. 1 is a schematic diagram of the non-aromatic purge step employed in a conventional cumene process.

As used herein, the term "$C_n$" compound wherein n is a positive integer, e.g., 1, 2, 3, 4, 5, means a compound having n number of carbon atom(s) per molecule. The term "$C_{n+}$" compound wherein n is a positive integer, e.g., 1, 2, 3, 4, 5, as used herein, means a compound having at least n number of carbon atom(s) per molecule. The term "$C_{n-}$" compound wherein n is a positive integer, e.g., 1, 2, 3, 4, 5, as used herein, means a compound having no more than n number of carbon atom(s) per molecule.

Described herein is a process for producing mono-alkylated aromatic products, particularly EB and cumene, by the alkylation of benzene with an alkylating agent in the presence of a first alkylation catalyst in a first or main alkylation reaction zone. In addition to unreacted benzene and the desired mono-alkylated aromatic product, the effluent from the main alkylation reaction zone comprises various heavier alkylaromatic compounds, particularly polyalkylated benzenes, such as di- and trialkylated compounds, as well as certain $C_5$, $C_6$ and/or $C_7$ non-aromatic impurities introduced into the system with the benzene feedstock and any non-aromatic compounds made in the main alkylation reaction zone and/or transalkylation reaction zone. Because of the difficulty of separating these non-aromatic components from benzene, they tend to build up in the recycle lines used to return the unreacted benzene to the first alkylation reaction zone. One or more non-aromatic purge streams are therefore removed from the first alkylation reaction effluent and are typically burnt as fuel or sold to a refinery at a heavily discounted price. However, as will be discussed in more detail below, in the present process, the non-aromatic purge stream(s) is fed to a second alkylation reaction zone where it is contacted with an alkylating agent in the presence of a second alkylation catalyst. In this way, at least part of the benzene in the non-aromatic purge can be converted to useful products thereby maximizing utilization of the benzene feedstock.

Feedstocks

Any commercially available benzene feedstock classified as suitable for alkylation can be used in the present process. Typically such feedstocks may contain up to 3000 ppm by weight of $C_5$, $C_6$ and/or $C_7$ non-aromatic components, such as but not limited to cyclopentane, n-pentane, methylpentanes, methylcylopentane, dimethylbutanes, cyclohexane, n-heptane, methylcyclohexane, methylhexanes, dimethylpentanes, 1,1-dimethylcyclopentane and ethylcyclopentane.

The present process can find utility with a wide range of alkylating agents, but has particular advantage with $C_2$ and $C_3$ alkylating agents. Suitable alkylating agents are olefins and alcohols, which may be linear, branched or cyclic. In some embodiments, the alkylating agent is a $C_2$ alkylating agent, such as ethylene or a $C_3$ alkylating agent, such as propylene and/or isopropanol. Preferably, the alkylating agent comprises propylene and/or isopropanol.

Main Alkylation Reaction

The main alkylation reaction may be carried out batchwise or on a continuous basis in any known reactor configuration. For example, the reaction may be carried out in one or more fixed or moving bed reactors. Fixed bed operation is preferred, typically with the alkylation reaction zone comprising one or a plurality of series-connected beds of alkylation catalyst.

The reaction conditions used to conduct the main alkylation reaction will depend on the particular alkylating agent employed, but suitable conditions are well within the ambit of anyone of ordinary skill in the art. For example, alkylation of benzene with ethylene to produce ethylbenzene is typically conducted at a temperature about 120° C. to 300° C., preferably, a temperature of from about 150° C. to 260° C., a pressure of 500 to 8300 kPa-a, preferably, a pressure of 1500 to 4500 kPa-a, so that at least part of the reaction mixture is maintained in the liquid phase during the process. Generally, the molar ratio of benzene to ethylene is from about 1 to about 100, preferably from about 20 to about 80. In the case of alkylation of benzene with propylene to produce cumene, typical reaction conditions include a temperature of about 20° C. to about 350° C., for example about 50° C. to about 300° C., such as about 100° C. to 280° C., and a pressure of about 100 kPa to about 20,000 kPa, for example about 500 kPa to about 10,000 kPa, so that at least part of the reaction mixture is maintained in the liquid phase during the process. Generally, the molar ratio of benzene to propylene is maintained within the range of about 1:1 to about 30:1, typically from 1.1:1 to 10:1.

Any known alkylation catalyst can be employed in the main alkylation reaction, but in most embodiments a heterogeneous solid acid catalyst, such as a molecular sieve, is preferred.

In one embodiment, the catalyst employed in the main alkylation reaction generally comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513) and mixtures thereof.

In addition to or instead of the MCM-22 family material, the main alkylation catalyst may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the main alkylation catalyst may comprise one or more large pore molecular sieves having a Constraint Index less than 2. Suitable large pore molecular sieves include zeolite beta, zeolite Y, Ultrastable Y (USY), Ultrahydrophobic Y (UHP-Y), Dealuminized Y (Deal Y), mordenite, ZSM-3, ZSM-4, ZSM-14, ZSM-18, ZSM-20 and mixtures thereof. Zeolite ZSM-3 is described in U.S. Pat. No. 3,415,736. Zeolite ZSM-4 is described in U.S. Pat. No. 4,021,947. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Zeolite Beta is described in U.S. Pat. Nos. 3,308,069, and Re. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 weight % and more usually, particularly, when the composite is prepared in the form of beads, in the range of about 2 to about 80 weight % of the composite.

Main Alkylation Reaction Effluent

In addition to the desired monoalkylated aromatic product, the effluent from the main alkylation reaction may contain significant quantities of unreacted benzene, together with smaller quantities of polyalkylated species, for example diisopropylbenzene (DIPB) and some triisopropylbenzene (TIPB) in a cumene process, and diethylbenzene (DEB) and some triethylbenzene (TEB) in an ethylbenzene process. Moreover, in some embodiments, the alkylation reaction effluent may also contain the $C_5$, $C_6$ and/or $C_7$ non-aromatic impurities introduced into the system with the benzene feedstock as well as any non-aromatic compounds made in the alkylation reactor. In the case of cumene production, examples of such $C_6$ non-aromatic by-products include 2,3-dimethylbutane, 2-methylpentane, 3-methylpentane and 2-ethyl-1-butene. The effluent from the main alkylation reaction is therefore fed to a separation system to allow recovery of the monoalkylated aromatic product and further processing of the by-products and impurities.

The separation system may include one or more benzene distillation columns, where unreacted benzene may be removed from the effluent as an overhead or side stream for recycle to the main alkylation reactor and/or to a transalkylation reactor (as described below). Lights and water may be removed as either an overhead distillate from the benzene column(s) or from a downstream lights column, that can also serve to dry makeup benzene, with the bottoms of the lights column being combined with the benzene column(s) overhead.

The bottoms from the benzene column(s) can then be fed to one or more monoalkylate distillation columns to recover the desired monoalkylated aromatic product. The bottoms from the monoalkylate column(s) contain the majority of the byproducts of the alkylation reaction heavier than the desired monoalkylate product. This bottoms stream may then be fed to one or more polyalkylate distillation columns to separate a polyalkylated aromatic product stream containing most of the dialkylated by-product and part of the trialkylated by-product, optionally for passage to a transalkylation reactor. The remainder of the trialkylated by-product and essentially all of the compounds heavier than the trialkylated by-product may be discharged at the bottoms of the polyalkylate column as residue.

In addition, to prevent build-up of non-aromatics in the benzene recycle, the separation system includes provision for removal of at least one non-aromatic purge stream from the alkylation reactor effluent, for example as an overhead stream from the benzene distillation column or as part of a benzene-containing side draw from the benzene distillation column or as an overhead distillate from a benzene lights column. The non-aromatic purge stream contains unreacted benzene as well as the $C_5$, $C_6$ and/or $C_7$ non-aromatic impurities to be purged and, as will be described in more detail below, is fed to a second alkylation reactor for conversion of at least part of the unreacted benzene to further mono- and polyalkylated product before the remainder of the purge stream is vented from the system.

Transalkylation Reaction

In some embodiments, the polyalkylated aromatic product stream recovered by the product separation system is fed to a transalkylation reactor, which may be separate from the main alkylation reactor, where the polyalkylated aromatic product is reacted with additional benzene in the presence of a transalkylation catalyst to convert at least part of the polyalkylated aromatic product to additional monoalkylated product. The transalkylation catalyst preferably comprises a molecular sieve selected from MCM-22, PSH-3, SSZ-25, MCM-36, MCM-49, MCM-56 and zeolite beta. In addition, the transalkylation catalyst may comprise ZSM-5, zeolite X, zeolite Y, or mordenite, such as TEA-mordenite. The transalkylation catalyst may be the same as or different from the alkylation catalyst. Suitable conditions for the transalkylation of both polyethylbenzenes and polyisopropylbenzenes with benzene include a temperature of 50° C. to 300° C., a pressure of 100 KPa to 20,000 KPa, a weight hourly space velocity of 0.2 to 20 on total feed and benzene/polyalkylate weight ratio 0.5:1 to 10:1. Typically, the transalkylation conditions are controlled such that the polyalkylated aromatic compounds and the benzene are at least partially or predominantly in the liquid phase.

In addition to the desired monoalkylated product, the effluent from the transalkylation reaction will normally contain unreacted polyalkylated product, unreacted benzene and, in some cases, additional non-aromatic hydrocarbons generated during the transalkylation reaction. Examples of such compounds include 2,3-dimethylbutane, 2-methylpentane, 3-methylpentane and 2-ethyl-1-butene. The transalkylation reaction effluent may then be fed to the product separation system described above to recover the additional monoalkylated product, separate the unreacted benzene and remove $C_5$, $C_6$ and/or $C_7$ non-aromatic hydrocarbons in the non-aromatic purge stream.

Alkylation of Non-Aromatic Purge Stream

In the present process, at least part of the non-aromatic purge stream removed from the main alkylation reactor effluent, and where applicable, the transalkylation reaction effluent, is supplied to at least one second alkylation reactor, separate from the main alkylation reactor, where the non-aromatic purge stream is contacted with an alkylating agent, preferably the same alkylating agent used in the main alkylation reactor(s), in the presence of a second alkylation catalyst under alkylation conditions effective to convert at least part of the benzene in the purge stream to mono- and polyalkylated benzenes. In some embodiments, water may be removed from the non-aromatic purge stream, for example, using an adsorbent, before the purge stream is fed to the second alkylation reactor. Typically, the non-aromatic purge stream fed to the second alkylation reactor comprises at least 5% by weight, or at least 10% by weight, such as at least 15% by weight, for example at least 20% by weight, of $C_5$, $C_6$ and/or $C_7$ non-aromatic hydrocarbons and up to 70% by weight, such as up to 60% by weight, for example up to 50% by weight, of $C_5$, $C_6$ and/or $C_7$ non-aromatic hydrocarbons. In some embodiments, the non-aromatic purge stream comprises at least 30% by weight, such as at least 40% by weight, for example at least 50% by weight, of benzene and up to 90% by weight, such as up to 80% by weight, for example up to 70% by weight, of benzene.

The conditions used in the second alkylation reactor can be the same as those employed in the main alkylation reactor. In some embodiments, particularly in the case of propylene as the alkylating agent, the conditions used in the second alkylation reactor comprise an inlet temperature in the range from 100° C. to 270° C., such as from 120° C. to 250° C., and a molar ratio of benzene to alkylating agent from 0.3:1 to 3:1, for example from 0.6:1 to 2:1, such as from 0.8:1 to 1.2:1. The pressure in the second alkylation reactor may be maintained such that the reactants and products are in the liquid phase.

The second alkylation catalyst can be selected from any of the catalysts listed above as suitable for the main alkylation reaction. In addition, the second alkylation reactor can contain a single bed of catalyst or multiple beds and can comprise more than one reactor connected in series or in parallel. In addition, since alkylation reactions are highly exothermic, part of the second reactor effluent can be cooled and recirculated back to the inlet of the second alkylation reactor.

The effluent of the second alkylation reactor comprises alkylbenzenes (mostly mono- and dialkylated species), unreacted benzene and $C_5$, $C_6$ and/or $C_7$ non-aromatic hydrocarbons. At least part of this effluent is fed to a non-aromatics purge column where the benzene and non-aromatics are removed as overhead and the alkylbenzenes leave as bottoms. The alkylbenzenes can then be fed back to the product separation system, via either the benzene column or the monoalkylate column, for recovery of the mono- and polyalkylated benzenes.

Part of the overhead of the non-aromatics purge column may be recycled to the second alkylation reactor, while the remainder is rejected from the system.

The invention will now be more particularly described with reference to the accompanying drawings.

FIG. 1 is a schematic diagram illustrating the non-aromatic purge step employed in a conventional cumene process. In the process shown in FIG. 1, the effluent from a cumene alkylation reactor (not shown) is fed by line 11 to a benzene column 12. Recycle benzene is removed from the benzene column 12 as a side stream 13 a few stages below the top of the column, allowing the $C_5$ and/or $C_6$ non-aromatic hydrocarbons to be concentrated in the distillate removed from the top of the column for purging via line 14. An additional purge may be taken via line 15 from the recycle benzene in side stream 13 to remove $C_7$ non-aromatic hydrocarbons that tend to have a higher concentration in the side stream 13 than the distillate in line 14. The benzene and $C_5$, $C_6$ and/or $C_7$ non-aromatic hydrocarbons contained in lines 14 and 15 are purged from the system resulting in loss of valuable benzene feedstock. Alkylated aromatics are recovered as a bottoms stream from the benzene column 12 via line 16.

Figure 2:
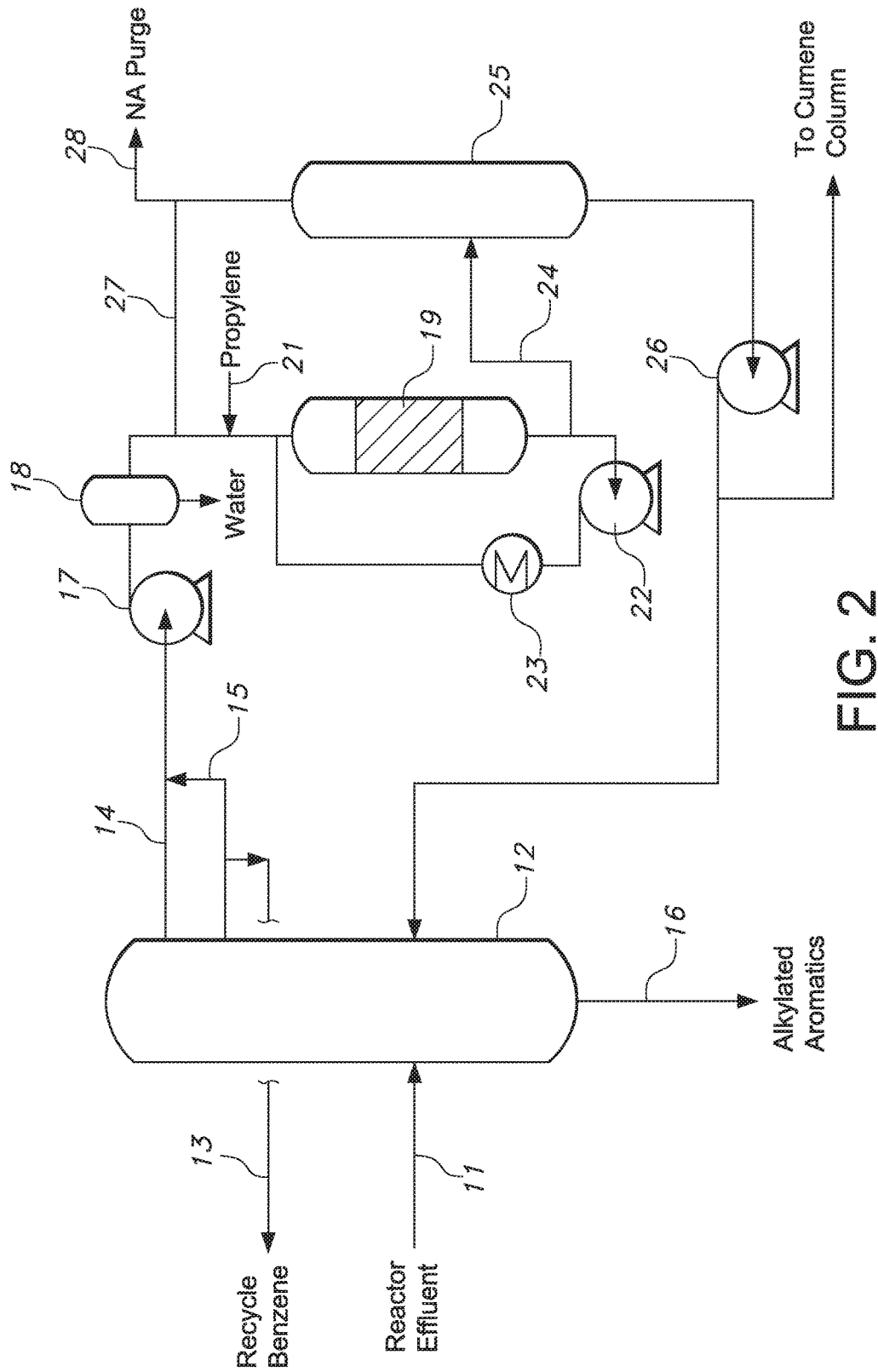
FIG. 2 is a schematic diagram of the non-aromatic purge step employed in a cumene process according to one embodiment of the present invention.

FIG. 2 is a schematic diagram of the non-aromatic purge step employed in a cumene process according to one embodiment of the present invention. Like numerals are used to designate like components in FIGS. 1 and 2. In the process shown in FIG. 2, the distillate in line 14 and the optional purge in line 15 are combined and, instead of being purged from the system, are fed via feed pump 17 through an optional drier 18 to a second alkylation reactor 19. Propylene is fed via line 21 to the reactor 19 which is maintained under conditions such that at least part of the benzene in the feed from lines 14 and 15 is alkylated to produce cumene and polypropylated benzenes.

Part of the effluent from the second alkylation reactor 19 is pumped through circulation pump 22 and cooler 23 back to the reactor 19 to control the inlet temperature of the reactor, while the remainder of the effluent is fed by line 24 to a non-aromatics purge column 25. Alkylated aromatics in the effluent from the second alkylation reactor 19 are recovered as a bottoms stream from the non-aromatics purge column 25 and are pumped by pump 26 either to the benzene column 12 or a cumene column (not shown). Non-aromatics and benzene in the effluent from the second alkylation reactor 19 are removed as distillate from the non-aromatics purge column 25 and either recycled via line 27 to the second alkylation reactor 19 or purged from the system through line 28.

The following non-limiting Examples are provided to further illustrate the process of the present invention.

Example 1

An alkylation test of non-aromatic purge stream with $C_3$ alkylating agent was carried out in a fixed bed reactor made from a ¾ inch (19 mm) diameter Schedule 40 Stainless Steel 316 pipe with a total length of 34 inches (864 mm). A storage tank was used for the non-aromatic purge stream and another tank was used for propylene. A positive displacement pump was used for feeding the non-aromatic purge stream into the reactor and another positive displacement pump was used for feeding propylene into the reactor. The flow rates of the non-aromatic purge stream and propylene were set by pump settings and monitored by electronic weight scales. The reactor operating conditions were controlled and monitored by an automatic control system. A portion of the reactor effluent was circulated back to the reactor inlet by a centrifugal pump to control the temperature rise across the catalyst bed below 20° C. The reactor pressure was controlled to maintain liquid phase operation. The feedstock and reactor effluent were analyzed by two Hewlett Packard 5890 Series II Gas Chromatographs, one equipped with a Chrompack CP-Wax 52CB column having an inside diameter of 0.25 mm, film thickness of 0.5 μm, and length of 60 meters, and the other one equipped with an Agilent DB-1 column having an inside diameter of 0.25 mm, film thickness of 0.5 μm, and length of 100 meters.

To conduct the test, 30 grams of an MCM-22 family catalyst was loaded into the fixed bed reactor. A non-aromatic purge stream comprising 80 wt % benzene and 20 wt % $C_6$ non-aromatic hydrocarbons was introduced into the reactor at about 56 grams per hour. The propylene feed was about 30 grams per hour. The feed benzene to propylene ratio was 0.8:1 molar, and the reactor inlet temperature was 128° C. The reactor effluent was found to comprise non-aromatic hydrocarbons, unconverted benzene, cumene, DIPB, TIPB, and heavy alkylated benzenes. The benzene conversion was 82% and benzene selectivity to isopropylbenzenes (including cumene, DIPB, and TIPB) was 99.0% molar.

Example 2

The same reactor setup, catalyst loading, and feedstock described in Example 1 were used in this example. The reactor inlet temperature was raised from 128° C. to 160° C. The benzene conversion increased from 82% to 84% and benzene selectivity to isopropylbenzenes was 99.1% molar.

Example 3

The same reactor setup, catalyst loading, and feedstock described in Example 1 were used in this example. The non-aromatic purge stream feed rate was raised from 56 to 84 grams per hour and the propylene feed was kept at about 30 grams per hour. The feed benzene to propylene ratio was 1.2:1 molar and the reactor inlet temperature was 128° C. The benzene conversion was 62% and benzene selectivity to isopropylbenzenes was 99.5% molar.

Example 4

The same reactor setup and catalyst loading described in Example 1 were used in this example. A non-aromatic purge stream comprising 60 wt % benzene and 40 wt % $C_6$ non-aromatic hydrocarbons was introduced into the reactor at about 111 grams per hour. The propylene feed was about 30 grams per hour. The feed benzene to propylene ratio was 1.2:1 molar and the reactor inlet temperature was 128° C. The benzene conversion was 62% and the benzene selectivity to isopropylbenzenes was 99.3% molar.

Example 5

The same reactor setup and catalyst loading described in Example 1 were used in this example. A non-aromatic purge stream comprising 80 wt % benzene, 19.4 wt % $C_6$ non-aromatic hydrocarbons, and 0.6 wt % isopropanol was introduced into the reactor at about 56 grams per hour. The isopropanol contained in the non-aromatic purge stream was used as part of the $C_3$ alkylating agent in this and the next three examples. Since isopropanol also produced water when it reacted with benzene to produce isopropylbenzenes, it also raised the water content in the reactor. The 0.6 wt % isopropanol in the non-aromatic purge stream was equivalent to about 0.2 wt % water in the same stream. The propylene feed was about 30 grams per hour. The feed benzene to propylene ratio was 0.8:1 molar and the reactor inlet temperature was 180° C. The benzene conversion was found to be 79% and the benzene selectivity to isopropylbenzenes was 98.5% molar.

Example 6

The same reactor setup, catalyst loading, and feedstock described in Example 5 were used in this example. The reactor inlet temperature was raised from 180° C. to 210° C. The benzene conversion increased from 79% to 82% and the benzene selectivity to isopropylbenzenes decreased slightly from 98.5% to 98.4% molar.

Example 7

The same reactor setup, catalyst loading, and feedstock described in Example 5 were used in this example. The non-aromatic purge stream feed rate was raised from 56 to 84 grams per hour and the propylene feed was kept at about 30 grams per hour. The feed benzene to propylene ratio was 1.2:1 molar and the reactor inlet temperature was 180° C. The benzene conversion was 61% and benzene selectivity to isopropylbenzenes was 99.2% molar.

Example 8

The same reactor setup and catalyst loading described in Example 1 were used in this example. A non-aromatic purge stream comprising 60 wt % benzene, 39.4 wt % $C_6$ non-aromatic hydrocarbons, and 0.6 wt % isopropanol was introduced into the reactor at about 111 grams per hour. The propylene feed was about 30 grams per hour. The feed benzene to propylene ratio was 1.2:1 molar and the reactor inlet temperature was 180° C. The benzene conversion was 60% and the benzene selectivity to isopropylbenzenes was 98.5% molar.

Example 9

A computer simulation of the following system was carried out. A non-aromatic hydrocarbon purge stream comprising 80 wt % benzene and 20 wt % $C_6$ non-aromatic hydrocarbons was fed into a second alkylation reactor operated at 160° C. and with a benzene to propylene molar ratio of 0.8:1. The reactor effluent was sent to stage 8 of a non-aromatic purge column comprised of 16 theoretical stages. The unreacted benzene and $C_6$ non-aromatic hydrocarbons were removed overhead. 81% of the benzene contained in the non-aromatic hydrocarbon purge stream was recovered as isopropylbenzenes in the column bottoms. These isopropylbenzenes can be recovered as additional cumene in downstream transalkylation reactor and distillation columns according to this invention. This example therefore demonstrated that benzene loss in the non-aromatic hydrocarbon purge stream can be reduced by 81% according to present invention.

Example 10

A computer simulation of the following system was carried out. A non-aromatic hydrocarbon purge stream comprising 80 wt % benzene and 20 wt % $C_6$ non-aromatic hydrocarbons was fed into a second alkylation reactor operated at 160° C. and with a benzene to propylene molar ratio of 0.8:1. The reactor effluent was sent to stage 8 of a non-aromatic purge column comprised of 16 theoretical stages. 67% of the unreacted benzene and $C_6$ non-aromatic hydrocarbons recovered overhead of the non-aromatic purge column was recycled back to the second alkylation reactor while the rest was purged from the system. 93% of the benzene contained in the non-aromatic hydrocarbon purge stream was recovered as isopropylbenzenes in the non-aromatic purge column bottoms. These isopropylbenzenes can be recovered as additional cumene in downstream transalkylation reactor and distillation columns according to present invention. This example therefore demonstrated that the benzene loss in the non-aromatic hydrocarbon purge stream can be reduced by 93% according to present invention.

The above examples demonstrate that the benzene loss in the non-aromatic hydrocarbon purge stream can be reduced by at least about 60 to 93% according to present invention, therefore significantly reducing the raw material cost for cumene production. With further optimization of the operating conditions of the second alkylation reactor and the recycle of unreacted benzene, the reduction of benzene loss according to present invention can be more than 93%, thus reducing the raw material cost for cumene production even more.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A method for producing a monoalkylated aromatic product, the method comprising:
   (a) contacting benzene and an alkylating agent with an alkylation catalyst in a first alkylation reaction zone under alkylation conditions to produce a first alkylation effluent comprising a first amount of the monoalkylated aromatic product, a first amount of polyalkylated aromatic product, unreacted benzene and $C_5$, $C_6$ and/or $C_7$ non-aromatic compounds;
   (b) removing a purge stream containing $C_5$, $C_6$ and/or $C_7$ non-aromatic compounds and unreacted benzene from the first alkylation effluent;
   (c) contacting at least part of the purge stream with a second alkylating agent in a second alkylation reaction zone in the presence of a second alkylation catalyst under alkylation conditions to produce a second alkylation effluent comprising a second amount of the monoalkylated aromatic product, a second amount of polyalkylated aromatic product and $C_5$, $C_6$ and/or $C_7$ non-aromatic compounds;
   (d) recovering the monoalkylated aromatic product from the first and second alkylation effluents; and
   (e) purging at least part of the $C_5$, $C_6$ and/or $C_7$ non-aromatic compounds in the second alkylation effluent.

2. A method according to claim 1, wherein the alkylating agent employed in each of (a) and (c) comprises a $C_2$ or a $C_3$ alkylating agent.

3. A method according to claim 1, wherein the alkylating agent employed in each of (a) and (c) comprises a $C_3$ alkylating agent.

4. A method according to claim 1, wherein the alkylating agent employed in each of (a) and (c) comprises propylene and/or isopropanol and the monoalkylated aromatic product comprises cumene.

5. A method according to claim 1, wherein the purge stream removed in (b) comprises at least 5% by weight of $C_5$, $C_6$ and/or $C_7$ non-aromatic compounds.

6. A method according to claim 1, wherein the purge stream removed in (b) comprises at least 5% by weight of $C_5$, $C_6$ and/or $C_7$ non-aromatic compounds selected from cyclopentane, n-pentane, methylpentanes, methylcyclopentane, cyclohexane, n-heptane, dimethylbutanes, 2-ethyl-1-butene, methylcyclohexane, methylhexanes, dimethylpentanes, 1,1-dimethylcyclopentane and ethylcyclopentane.

7. A method according to claim 1 and further comprising:
   (f) supplying at least part of the first alkylation effluent to a first distillation apparatus; and
   (g) recovering monoalkylated and polyalkylated aromatic product as a bottom stream of the first distillation apparatus, unreacted benzene as a side stream of the first distillation apparatus and the purge stream as an overhead stream of the first distillation apparatus.

8. A method according to claim 1 and further comprising:
   (f) supplying at least part of the first alkylation effluent to a first distillation apparatus;
   (g) recovering monoalkylated and polyalkylated aromatic product as a bottom stream of the first distillation apparatus and unreacted benzene and $C_5$, $C_6$ and/or $C_7$ non-aromatic compounds as an overhead stream of the first distillation apparatus;
   (h) recovering benzene and a distillate fraction from the overhead stream; and
   (i) supplying at least part of the distillate fraction to a lights column to separate the distillate fraction into a $C_4$ lights stream and the purge stream.

9. A method according to claim 7 and further comprising:
   (j) supplying at least part of the second alkylation effluent to a second distillation apparatus;
   (k) recovering monoalkylated and polyalkylated aromatic product as a bottom stream and $C_5$, $C_6$ and/or $C_7$ non-aromatic compounds as an overhead stream; and
   (l) directing at least part of the bottom stream recovered in (k) to the first distillation apparatus.

10. A method according to claim 1, wherein water is removed from the non-aromatics purge stream produced in (b) prior to the contacting (c).

11. A method according to claim 1, wherein a portion of the second alkylation effluent is recycled to an inlet of the second alkylation reaction zone.

12. A method according to claim 1, wherein a portion of the second alkylation effluent is recycled to an inlet of the second alkylation reaction zone via a cooler.

13. A method according to claim 1, wherein the alkylation conditions in the contacting (c) comprise an inlet temperature in the range from 100° C. to 270° C.

14. A method according to claim 1, wherein the alkylation conditions in the contacting (c) comprise a molar ratio of benzene to alkylating agent from 0.3:1 to 3:1.

15. A method according to claim 1 and further comprising:
   (m) recovering polyalkylated aromatic product from the first and second alkylation effluents; and
   (n) contacting the polyalkylated aromatic product with benzene in the presence of a transalkylation catalyst in a transalkylation reaction zone under transalkylation conditions to produce a transalkylation effluent comprising the monoalkylated aromatic product; and
   (o) recovering monoalkylated aromatic product from the transalkylation effluent.

* * * * *